United States Patent
Ma et al.

(10) Patent No.: US 11,760,700 B2
(45) Date of Patent: Sep. 19, 2023

(54) METHOD OF CONTINUOUSLY CONVERTING KITCHEN WASTE USING THREE ENVIRONMENTAL INSECTS

(71) Applicant: XINJIANG AGRICULTURAL UNIVERSITY, Urumqi (CN)

(72) Inventors: De Ying Ma, Urumqi (CN); Guang Jie Zhang, Urumqi (CN); Song Qiang, Urumqi (CN)

(73) Assignee: XINJIANG AGRICULTURAL UNIVERSITY, Urumqi (CN)

( * ) Notice: Subject to any disclaimer, the term of this patent is extended or adjusted under 35 U.S.C. 154(b) by 287 days.

(21) Appl. No.: 17/084,658

(22) Filed: Oct. 30, 2020

(65) Prior Publication Data
US 2021/0130248 A1   May 6, 2021

(30) Foreign Application Priority Data
Oct. 31, 2019   (CN) .......................... 201911050399.3

(51) Int. Cl.
*C05F 9/04* (2006.01)
*C05F 17/05* (2020.01)
*A01K 67/033* (2006.01)

(52) U.S. Cl.
CPC .............. *C05F 9/04* (2013.01); *A01K 67/033* (2013.01); *C05F 17/05* (2020.01)

(58) Field of Classification Search
None
See application file for complete search history.

(56) References Cited

FOREIGN PATENT DOCUMENTS

| CN | 108372187 A | * | 8/2018 | ................ C05F 9/02 |
| CN | 109500047 A | * | 3/2019 | ................ C05F 3/00 |

* cited by examiner

*Primary Examiner* — Wayne A Langel

(57) ABSTRACT

The present disclosure provides a method of continuously converting kitchen waste using three environmental insects, including following steps: pre-solid-liquid separating and removing impurities of kitchen waste using feeding and drainage characteristics of *Tenebrio molitor*, *Hermetia illucens*, and *Protaetia brevitarsis* Lewis; feeding larvae of the *Tenebrio molitor* with solids added with crushed wheat bran in a day, and completely digesting the solids added with the crushed wheat bran in the day; and adding liquid with dung-sand of the *Tenebrio molitor*, crop straw dry powder, and probiotics to ferment, converting the fermented liquid added with the dung-sand of the *Tenebrio molitor*, the crop straw dry powder, and the probiotics by larvae of the *Hermetia illucens*, and then converting and digesting the fermented liquid added with the dung-sand of the *Tenebrio molitor*, the crop straw dry powder, and the probiotics by mixing larvae of the *Protaetia brevitarsis* Lewis.

7 Claims, 2 Drawing Sheets

METHOD OF CONTINUOUSLY CONVERTING KITCHEN WASTE USING THREE ENVIRONMENTAL INSECTS

TECHNICAL FIELD

The present disclosure relates to a field of ecological agriculture circulation, and in particular to a method of continuously converting kitchen waste using three environmental insects.

BACKGROUND

At present, the prior art closest to the present disclosure is as follows: China is a large consumer group with approximately a population of 1.4 billion. According to accounting, amount of kitchen waste produced per day is more than 60 million tons, while the amount of the kitchen waste annually produced meets rations of 200 million people per year. The kitchen waste has dual nature of resource and pollution, and how to realize reduction, harmlessness, and resource treating of a large amount of the kitchen waste is a worldwide problem. Currently, conversion treating technology of the kitchen waste is mainly sanitary landfill and biological conversion. However, due to a fact that the amount of the kitchen waste is huge and limited by available landfill resources and containment volume, the sanitary landfill in each place faces a dilemma of approaching saturation. Rapid spreading of African swine fever throughout countries is greatly associated with that pigs are fed by the kitchen waste, the Ministry of Agriculture and Rural Affairs has forbidden feeding the pigs by the kitchen waste, thus, directly converting the kitchen waste into feed of livestock is forbidden. High-salt, high-oil, and high-water characteristics of the kitchen waste not only makes anaerobic biogas production and aerobic composting technology large in front-end input, but also exists problems of a fermentation effect is poor, biogas residue and fertilizer-making product are high in salt content, an applying effect as organic fertilizer is poor, product price is low, and user acceptance rate is low, etc., which can only be supported to operate by national subsidy. Environmental insects are sweepers of nature, having advantages of large feed intake, strong reproductive capacity, high conversion efficiency, no secondary pollution, intensive three-dimensional breeding, and the like. The environmental insects are presently and maturely used in converting the kitchen waste are *Tenebrio molitor, Hermetia illucens* (*H. illucens*), *Protaetia brevitarsis* Lewis (*P. brevitarsis*), *Periplaneta americana*, etc. The described environmental insects are used in conversion treatments of the kitchen waste, livestock and poultry manure, and crop straw, which seems achieves some success, but are still limited by difference between degree of awareness of environmental insect conversion organic waste characteristics with industry and degree of mastery of insect breeding technologies and conversion treatment organic waste technologies. The prior art mostly uses a single environmental insect to convert the kitchen waste, converting the kitchen waste by two environmental insects looks fresh. The kitchen waste is complex in composition, which requests high pretreatment conditions in using the single environmental insect, and exists disadvantages that a conversion period is long, the conversion is incomplete, and an investment cost is high, etc.

Based on above, problems existing in the prior art is as following: The sanitary landfill of the kitchen sanitary faces a dilemma of having no place to fill, the anaerobic biogas production and the aerobic composting are maintained against the national subsidy, and conversion efficiency and benefit of the single environmental insect are low. The industry is limited by degree of awareness of environmental insect characteristics and degree of mastery of a technology of large-scale conversion on the kitchen waste using the environmental insects. The prior art does not combine three environmental insects of the *Tenebrio molitor*, the *H. illucens*, and the *P. brevitarsis* to convert and treat the kitchen waste.

Difficulties of solving the described technical problems are as following: The kitchen waste is complex in composition and is huge in body amount. Aiming at the complex composition, there must be a system solution with an excellent practical operation; aiming at the huge body amount, there must be a conversion technology system with efficient supporting to support. Fully excavating characteristics of the environmental insects, and organically combining complementary advantages, mature technologies, and large-scale production of the three environmental insects, may shoulder this responsibility.

Significance of solving the described technical problems is as following: There are strong accumulation in aspects of theoretical researches, the large-scale production, and practice of converting organic waste of the three environmental insects of the *Tenebrio molitor*, the *H. illucens*, and the *P. brevitarsis*, in particular to a field of the *Tenebrio molitor* and the *P. brevitarsis*, there is a proximal 20 years of continuous research and practice. Firm foundation and urgent needs of reality help team innovate and perform a research and practice of combining the three environmental insects of the *Tenebrio molitor*, the *H. illucens*, and the *P. brevitarsis* to convert and treat the kitchen waste, and high-speed, high-efficiency, high-value conversion of the kitchen waste is finally realized to provide an innovative way for efficiently utilizing resources of the kitchen waste. Rear-end of the anaerobic biogas production and the aerobic composting technology gets a high value of insect protein extending to ecological planting and breeding industry, and dung-sand of larvae of the *P. brevitarsis* extends to ecological planting industry, which contributes to green development of agriculture and further improves quality and efficiency of the agriculture.

SUMMARY

Aiming at problems in the prior art, the present disclosure provides a method of continuously converting kitchen waste using three environmental insects.

The method of continuously converting kitchen waste using three environmental insects is summarized as follows: pre-solid-liquid separating and removing impurities of kitchen waste using feeding and drainage characteristics of *Tenebrio molitor*, *H. illucens*, and *P. brevitarsis*; feeding larvae of the *Tenebrio molitor* with solids added with crushed wheat bran in a day, and completely digesting the solids added with the crushed wheat bran in the day; adding liquid with dung-sand of the *Tenebrio molitor*, crop straw dry powder, and probiotics to ferment, converting the fermented liquid added with the dung-sand of the *Tenebrio molitor*, the crop straw dry powder, and the probiotics by larvae of the *H. illucens*, and then converting and digesting the fermented liquid added with the dung-sand of the *Tenebrio molitor*, the crop straw dry powder, and the probiotics by mixing larvae of the *P. brevitarsis*.

Furthermore, the method of continuously converting kitchen waste using three environmental insects includes following steps:

First step, hermetically transporting the kitchen waste to a base where continuously converting the kitchen waste using three environmental insects, separating out the solids by a solid-liquid separating machine, and separating the liquid into a fermentation pool.

Second step, selecting the solids and removing the impurities from the solids, adding the solids with 15%-20% wheat bran, mixing and crushing the solids and the wheat bran by a stirrer, mixing with 40%-45% water content; feeding 1.5 cm-2.5 cm larvae of the *Tenebrio molitor* with the solids added with crushed wheat bran in the day, eating up feeding amount by the larvae of the *Tenebrio molitor* within 4 hours, the feeding amount is in a standard of 80 cm*40 cm*8 cm per box; completely digesting the solids added with the crushed wheat bran more than 95% by the larvae of the *Tenebrio molitor* in the day; sieving residual organic matters and dung-sand per week, mixing and crushing the residual organic matters, using the residual organic matters and the dung-sand as raw materials for fermenting the liquid of the kitchen waste; stopping feeding when the larvae of the *Tenebrio molitor* reach 2.7 cm-2.9 cm mature larvae, harvesting insect bodies, and replenishing young larvae meeting conversion conditions.

Third step: on the same day, adding 10% dung-sand of the *Tenebrio molitor*, and crushed residual organic matters, 15% crop straw dry powder, 2‰ probiotics, and 1‰ decomposition microbial slot type aerobic into the fermentation pool to ferment for 24 hours, at this time, water content of materials in the fermentation pool is at 60%-70%; converting the materials by 5-day-old larvae of the *H. illucens* for 7 days, adding 2.0 cm-3.5 cm larvae of the *P. brevitarsis* into the fermentation pool to continuously mix and convert for 2 days to completely digest the kitchen waste; continuously replenishing two kinds of the larvae of the *H. illucens* and the *P. brevitarsis*, and harvesting mature larvae of the *H. illucens* and the *P. brevitarsis* and dung-sand of the *P. brevitarsis*.

Fourth step: harvesting the mature larvae of the three environmental insects to leave sufficient seed sources for breeding.

Furthermore, in the third step, tiling the materials of 15 cm-20 cm in a cultivation pool, height of the cultivation pool is 30 cm, width of the cultivation pool is 100 cm, and length of the cultivation pool is not limited; putting 15 kg-20 kg 5-day-old larvae of the *H. illucens* into per 1 ton materials, putting the larvae of the *H. illucens* at once, putting the materials according to proportion of 1:2 at twice, when height of the materials putted first time drops to 10 cm, putting the materials second time; converting the materials in the cultivation pool for 7 days, putting 10 kg-20 kg and 2.0 cm-3.5 cm larvae of the *P. brevitarsis* in the cultivation pool, mixing and converting the larvae of the *H. illucens* and the larvae of the *P. brevitarsis* for 2 days, and digesting mixtures of residual materials and excrement of the *H. illucens* by the larvae of the *P. brevitarsis*.

Furthermore, in the third step, separating the two kinds of insect bodies and dung-sand of the *H. illucens* and the *P. brevitarsis* by 4 mesh separation sieve and 8 mesh separation sieve to harvest the mature larvae of the *H. illucens* and the dung-sand of the *P. brevitarsis*; re-putting the larvae of the *P. brevitarsis* into a *H. illucens* conversion pool meeting putting batch conditions; until the larvae of the *P. brevitarsis* grow into 3.7 cm-3.9 cm mature larvae, harvesting the mature larvae of the *P. brevitarsis*, and replenishing young larvae of the *P. brevitarsis* meeting conversion conditions.

Furthermore, crop straws used in the method of continuously converting kitchen waste using the three environmental insects are wheat, corn, rice, peanut straw, or vegetable seeding.

Another object of the present disclosure is to provide insect source protein feed based on the method of continuously converting kitchen waste using the three environmental insects. Steps of forming the insect source protein feed is as follows: harvesting the mature larvae of the three environmental insects to leave the sufficient seed sources for breeding, drying the mature larvae of the three environmental insects through microwave, then crushing the dried mature larvae of the three environmental insects, sieving the crushed mature larvae of the three environmental insects through 40 mesh separation sieve, then adding the mature larvae of the three environmental insects into compound feed with proportion of 2%-15% to form the insect source protein feed.

Another object of the present disclosure is to provide the insect source protein feed to apply to special economic animal breeding such as cats, dogs, ornamental fish, lobster shrimps, crabs, etc.

Another object of the present disclosure is to provide the insect source protein feed to apply to livestock and poultry ecological breeding.

Another object of the present disclosure is to provide an insect manure-based biological fertilizer prepared in the method of continuously converting kitchen waste using three environmental insects, the insect manure-based biological fertilizer is prepared by adding 5%-10% macroelements and a proper proportion of trace elements in the harvested dung-sand of the larvae of the *P. brevitarsis*.

Another object of the present disclosure is to provide the insect manure-based biological fertilizer to apply to ecological planting industry In summary, the present disclosure pre-solid-liquid separates and removing impurities of the kitchen waste using the feeding and drainage characteristics of the *Tenebrio molitor*, the *H. illucens*, and the *P. brevitarsis* larvae of the *Tenebrio molitor* are fed with the solids added with the crushed wheat bran in a day, and the solids added with the crushed wheat bran are completely digested in the day. The liquid is added with the dung-sand of the *Tenebrio molitor*, crop straw dry powder, and probiotics to ferment for 1 day. The fermented liquid added with the dung-sand of the *Tenebrio molitor*, the crop straw dry powder, and the probiotics is converted by larvae of the *H. illucens* for 7 days, and then the fermented liquid added with the dung-sand of the *Tenebrio molitor*, the crop straw dry powder, and the probiotics is converted and digested by mixing larvae of the *P. brevitarsis* for 2 days. A conversion cycle only takes 10 days. Further, insect bodies of the three environmental insects and the dung-sand of the *P. brevitarsis* having wide applying prospect in the ecological planting and breeding industry are obtained, which realizes high-speed, high-efficiency, high-value conversion of the kitchen waste. The insect source protein feed formed by drying the mature larvae of the three environmental insects through microwave is applied to the special economic animal breeding and the livestock and the poultry ecological breeding, and the insect manure-based biological fertilizer made of the dung-sand of the larvae of the *Potosia brevitars* is applied to the ecological planting industry, which innovates and realizes efficient utilization of the kitchen waste and form a benign circulation industry chain of win-win economic, social, and ecological benefits.

DETAILED DESCRIPTION

In order to make the purpose, technical solutions, and advantages of the present disclosure clearer, the present disclosure will be described in further detail below with reference to embodiments. It should be understood that the specific embodiments described below are only used to explain the present disclosure, and are not intended to limit the present disclosure.

Aiming at problems existing in the prior art, the present disclosure provides a method of continuously converting kitchen waste using three environmental insects. The present disclosure is described in detail below in connection with the accompanying drawings.

Figure 1:
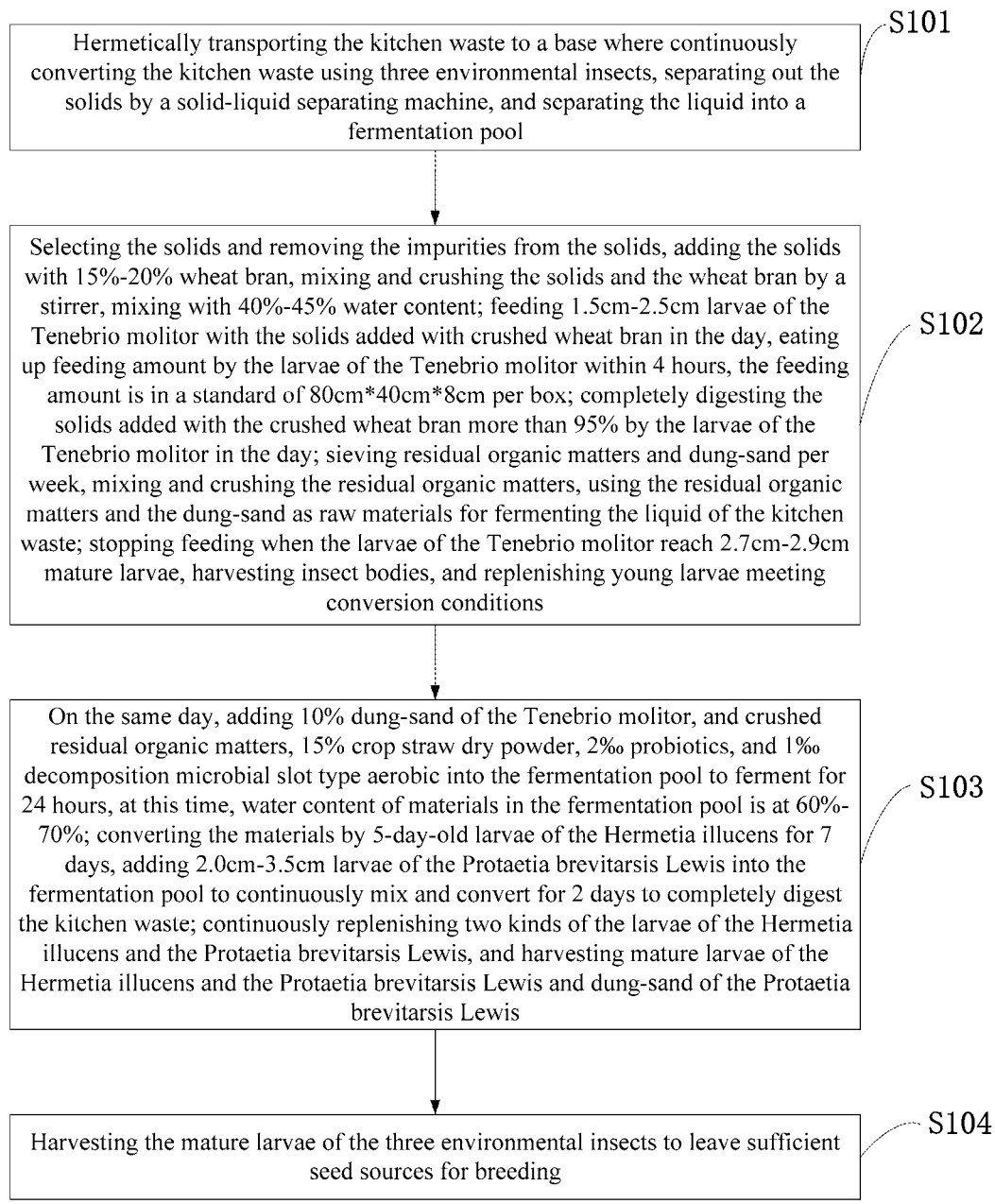
FIG. 1 is a flow chart of a method of continuously converting kitchen waste using three environmental insects according to one embodiment of the present disclosure.
Figure 2:
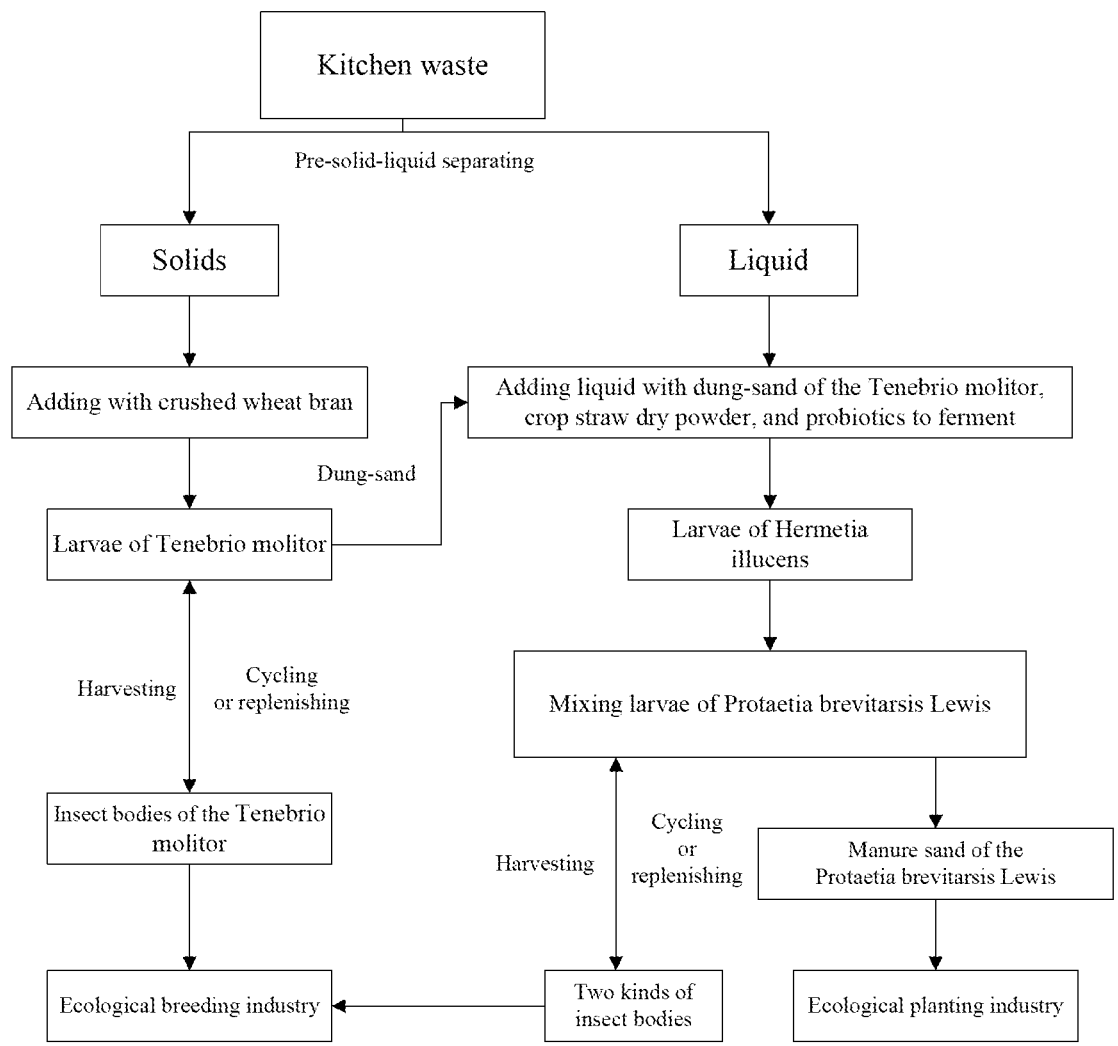
FIG. 2 is a flow chart of realizing the method of continuously converting kitchen waste using three environmental insects according to one embodiment of the present disclosure.

As shown in FIG. 1, in one embodiment, the present disclosure provides the method of continuously converting kitchen waste using three environmental insects, including following steps:

S101: hermetically transporting kitchen waste to a base where continuously converting the kitchen waste using three environmental insects, separating out solids by a solid-liquid separating machine, and separating liquid into a fermentation pool.

S102: selecting the solids and removing the impurities from the solids, adding the solids with 15%-20% wheat bran, mixing and crushing the solids and the wheat bran by a stirrer, mixing with 40%-45% water content; feeding 1.5 cm-2.5 cm larvae of the *Tenebrio molitor* with the solids added with crushed wheat bran in the day, eating up feeding amount by the larvae of the *Tenebrio molitor* within 4 hours, the feeding amount is in a standard of 80 cm*40 cm*8 cm per box; completely digesting the solids added with the crushed wheat bran more than 95% by the larvae of the *Tenebrio molitor* in the day; sieving residual organic matters and dung-sand per week, mixing and crushing the residual organic matters, using the residual organic matters and the dung-sand as raw materials for fermenting the liquid of the kitchen waste; stopping feeding when the larvae of the *Tenebrio molitor* reach 2.7 cm-2.9 cm mature larvae, harvesting insect bodies, and replenishing young larvae meeting conversion conditions.

S103: on the same day, adding 10% dung-sand of the *Tenebrio molitor*, and crushed residual organic matters, 15% crop straw dry powder, 2‰ probiotics, and 1‰ decomposition microbial slot type aerobic into the fermentation pool to ferment for 24 hours, at this time, water content of materials in the fermentation pool is at 60%-70%; converting the materials by 5-day-old larvae of the *H. illucens* for 7 days, adding 2.0 cm-3.5 cm larvae of the *P. brevitarsis* into the fermentation pool to continuously mix and convert for 2 days to completely digest the kitchen waste; continuously replenishing two kinds of the larvae of the *H. illucens* and the *P. brevitarsis*, and harvesting mature larvae of the *H. illucens* and the *P. brevitarsis* and dung-sand of the *P. brevitarsis*.

S104: harvesting the mature larvae of the three environmental insects to leave sufficient seed sources for breeding.

In one embodiment, in the S103, tiling the materials of 15 cm-20 cm in a cultivation pool, height of the cultivation pool is 30 cm, width of the cultivation pool is 100 cm, and length of the cultivation pool is not limited; putting 15 kg-20 kg 5-day-old larvae of the *H. illucens* into per 1 ton materials, putting the larvae of the *H. illucens* at once, putting the materials according to proportion of 1:2 at twice, when height of the materials putted first time drops to 10 cm, putting the materials second time; converting the materials in the cultivation pool for 7 days, putting 10 kg-20 kg and 2.0 cm-3.5 cm larvae of the *P. brevitarsis* in the cultivation pool, mixing and converting the larvae of the *H. illucens* and the larvae of the *P. brevitarsis* for 2 days, and digesting mixtures of residual materials and excrement of the *H. illucens* by the larvae of the *P. brevitarsis*. At this time, only insect bodies of larvae of the *H. illucens* and the *P. brevitarsis* and the granular dung-sand of the *P. brevitarsis* are left in the cultivation pool.

In one embodiment, in the S103, separating the two kinds of insect bodies and dung-sand of the *H. illucens* and the *P. brevitarsis* by 4 mesh separation sieve and 8 mesh separation sieve to harvest the mature larvae of the *H. illucens* and the dung-sand of the *P. brevitarsis*; re-putting the larvae of the *P. brevitarsis* into a *H. illucens* conversion pool meeting putting batch conditions; until the larvae of the *P. brevitarsis* grow into 3.7 cm-3.9 cm mature larvae, harvesting the mature larvae of the *P. brevitarsis*, and replenishing young larvae of the *P. brevitarsis* meeting conversion conditions.

In one embodiment, crop straws used in the method of continuously converting kitchen waste using the three environmental insects are wheat, corn, rice, peanut straw, or vegetable seeding, length of dry powder is between 0.1 cm and 1.0 cm, the probiotics adopts golden feed starter produced by Kangyuan Oasis Biotechnology (Beijing) Co., Ltd., the decomposition microbial adopts RW rot promoter produced by Hebei Renyuan Biotechnology Development Co., Ltd.

In one embodiment, the insect source protein feed formed by drying the mature larvae of the three environmental insects through microwave is applied to the special economic animal breeding and the livestock and the poultry ecological breeding, so that survival rate of feeding animals and quality of breeding are improved. The harvested dung-sand of the *P. brevitarsis* is dried and odorless grey black long elliptical particles, containing rich organic matters and nutrient elements. The harvested dung-sand of the *P. brevitarsis* further contains beneficial bacteria beneficial to crop growth, where the beneficial bacteria are featural biological fertilizer very good in quality. The harvested dung-sand of the *P. brevitarsis* is applied to the ecological planting industry, which has good yield increasing and quality improvement effects on tubers and roots of garlic, Chinese chives, and potatoes, etc.

The present disclosure aims at characteristics of complex composition and high water content of the kitchen waste, pre-solid-liquid separating and removing impurities of the kitchen waste using the feeding and drainage characteristics of the *Tenebrio molitor*, the *H. illucens*, and the *P. brevitarsis*, and then separately converting the solids and the liquid. Each batch of the kitchen waste takes 10 days as a continuous conversion cycle, finally, completely digesting the kitchen waste is realized and the insect bodies of the three environmental insects and the dung-sand of the *P. brevitarsis* are obtained. The insect bodies serving as the insect source protein feed are applied to the ecological breeding industry. The dung-sand preparing for the insect manure-based biological fertilizer is applied to the ecological planting industry. Thus, an ecological circulation industry chain of "kitchen waste-three environmental insects-insect bodies and dung-sand-ecological planting and breeding industry-consumers-kitchen waste" is formed.

The present disclosure harvests mature larvae of the three environmental insects to leave the sufficient seed sources for breeding, so that the matched young larvae are continuously provided for a conversion technology system to realize continuous conversion of the kitchen waste whole the year. The insect source protein feed formed by drying the mature larvae of the three environmental insects through microwave is applied to the special economic animal breeding and the livestock and the poultry ecological breeding. The harvested dung-sand of the *P. brevitarsis* is dried and odorless grey black long elliptical particles, containing rich organic matters and nutrient elements. The harvested dung-sand of the *P. brevitarsis* further contains beneficial bacteria beneficial to crop growth, where the beneficial bacteria are featural biological fertilizer very good in quality and are suitable for the ecological planting industry. The kitchen waste is converted in combination with the three environmental insects, characteristics of the *Tenebrio molitor* where the *Tenebrio molitor* eat fluid but excrete solids, the *H. illucens* where the *H. illucens* is highly resistant to the water content but excreta of the *H. illucens* is not shaped, and the *P. brevitarsis* where the *P. brevitarsis* is strong in conversion force to feces and high-fiber materials and the dung-sand of the *P. brevitarsis* is in a granular shape are combined to give full play to a synergistic effect of the characteristics of the three environmental insects, which ensures high-speed, high-efficiency, high-value conversion of the kitchen waste in a condition of less auxiliary material addition, low process energy consumption, short conversion period, and no secondary pollution.

Conversion data is indicated as follows: One 1000 m^2 plant may convert 60 tons kitchen waste per month, the 60 tons kitchen waste adds 12 tons crop straws to produce about 4 tons insect bodies and 18 tons dung-sand of the *P. brevitarsis*. At present an average market price of the insect bodies is $1492 per ton, a market price of the *Potosia brevitars* is $149 per ton. These two insect products may generate economic benefits of $8954 per month only as a commodity.

Actual application of the insect source protein feed is shown as follows: When 5% insect dry power raw materials are added into meat small chicken compound feed, meat small chicken breeding rate may reach 95%, and ratio of the meat small chicken breeding rate is increased by about 6%. When 3% insect dry powder raw materials are added into the meat middle chicken compound feed, the meat middle chicken may be incubated in advance for one week, and quality and flavor of which are better, thus, economic benefits are increased by approximately 2 times.

Actual application of the insect manure-based biological fertilizer is shown as follows: In a garlic plot test, when insect manure-based biological fertilizer serves as base fertilizer and is applied at a time of 1.50 kg/m^2, an experimental group may be increased by more than 25% compared with a control group in a same year. In a potato plot test, when the insect manure-based biological fertilizer serves as the base fertilizer and is applied at a time of 1.0 kg/m^2, the experimental group is increased by more than 30% compared with the control group in the same year, in addition, commodity potato rate is increased by more than 10%.

The above are merely the preferred embodiments of the present disclosure and are not intended to limit the present disclosure. Any modification, equivalent replacement and improvement made within spirit and principle of the present disclosure shall be included in protection scopes of the present disclosure.

What is claimed is:

1. A method of continuously converting kitchen waste using three environmental insects, comprising:
   pre-solid-liquid separating and removing impurities of kitchen waste using feeding and drainage characteristics of *Tenebrio molitor*, *Hermetia illucens*, and *Protaetia brevitarsis* Lewis;
   feeding larvae of the *Tenebrio molitor* with solids added with crushed wheat bran in a day, and completely digesting the solids added with the crushed wheat bran in the day; and
   adding, to the separated liquid, a liquid containing dung-sand of the *Tenebrio molitor*, crop straw dry powder and probiotics to ferment, converting the fermented liquid added with the dung-sand of the *Tenebrio molitor*, the crop straw dry powder, and the probiotics by larvae of the *Hermetia illucens*, and converting and digesting the fermented liquid added with the dung-sand of the *Tenebrio molitor*, the crop straw dry powder, and the probiotics by mixing larvae of the *Protaetia brevitarsis* Lewis.

2. The method of continuously converting kitchen waste using three environmental insects according to claim 1, wherein the method of continuously converting kitchen waste using three environmental insects comprises following steps:
   first step, hermetically transporting the kitchen waste to a base where continuously converting the kitchen waste using three environmental insects, separating out the solids by a solid-liquid separating machine, and separating the liquid into a fermentation pool;
   second step: selecting the solids and removing the impurities from the solids, adding the solids with 15%-20% wheat bran, mixing and crushing the solids and the wheat bran by a stirrer, mixing with 40%-45% water content; feeding 1.5 cm-2.5 cm larvae of the *Tenebrio molitor* with the solids added with crushed wheat bran in the day, eating up feeding amount by the larvae of the *Tenebrio molitor* within 4 hours, the feeding amount is in a standard of 80 cm*40 cm*8 cm per box; completely digesting the solids added with the crushed wheat bran more than 95% by the larvae of the *Tenebrio molitor* in the day; sieving residual organic matters and dung-sand per week, mixing and crushing the residual organic matters, using the residual organic matters and the dung-sand as raw materials for fermenting the liquid of the kitchen waste; stopping feeding when the larvae of the *Tenebrio molitor* reach 2.7 cm-2.9 cm mature larvae, harvesting insect bodies, and replenishing young larvae meeting conversion conditions;
   third step: on the same day, adding 10% dung-sand of the *Tenebrio molitor*, and crushed residual organic matters, 15% crop straw dry powder, 2‰ probiotics, and 1‰ decomposition microbial slot type aerobic into the fermentation pool to ferment for 24 hours, at this time, water content of materials in the fermentation pool is at 60%-70%; converting the materials by 5-day-old larvae of the *Hermetia illucens* for 7 days, adding 2.0 cm-3.5 cm larvae of the *Protaetia brevitarsis* Lewis into the fermentation pool to continuously mix and convert for 2 days to completely digest the kitchen waste; continuously replenishing two kinds of the larvae of the

*Hermetia illucens* and the *Protaetia brevitarsis* Lewis, and harvesting mature larvae of the *Hermetia illucens* and the *Protaetia brevitarsis* Lewis and dung-sand of the *Protaetia brevitarsis* Lewis; and fourth step: harvesting the mature larvae of the three environmental insects to leave sufficient seed sources for breeding.

3. The method of continuously converting kitchen waste using three environmental insects according to claim 2, wherein in the fourth step, harvesting the mature larvae of the three environmental insects to leave the sufficient seed sources for breeding, drying the mature larvae of the three environmental insects through microwave, then processing the mature larvae of the three environmental insects to form insect source protein feed.

4. The method of continuously converting kitchen waste using three environmental insects according to claim 3, wherein the insect source protein feed is applied to economic animal breeding and livestock and poultry ecological breeding.

5. The method of continuously converting kitchen waste using three environmental insects according to claim 2, wherein in the third step, tiling the materials of 15 cm-20 cm in a cultivation pool, height of the cultivation pool is 30 cm, width of the cultivation pool is 100 cm, and length of the cultivation pool is not limited; putting 15 kg-20 kg 5-day-old larvae of the *Hermetia illucens* into per 1 ton materials, putting the larvae of the *Hermetia illucens* at once, putting the materials according to proportion of 1:2 at twice, when height of the materials putted first time drops to 10 cm, putting the materials second time; converting the materials in the cultivation pool for 7 days, putting 10 kg-20 kg and 2.0 cm-3.5 cm larvae of the *Protaetia brevitarsis* Lewis in the cultivation pool, mixing and converting the larvae of the *Hermetia illucens* and the larvae of the *Protaetia brevitarsis* Lewis for 2 days, and digesting mixtures of residual materials and excrement of the *Hermetia illucens* by the larvae of the *Protaetia brevitarsis* Lewis.

6. The method of continuously converting kitchen waste using three environmental insects according to claim 2, wherein in the third step, separating the two kinds of insect bodies and dung-sand of the *Hermetia illucens* and the *Protaetia brevitarsis* Lewis by 4 mesh separation sieve and 8 mesh separation sieve to harvest the mature larvae of the *Hermetia illucens* and the dung-sand of the *Protaetia brevitarsis* Lewis; re-putting the larvae of the *Protaetia brevitarsis* Lewis into a *Hermetia illucens* conversion pool meeting putting batch conditions; until the larvae of the *Protaetia brevitarsis* Lewis grow into 3.7 cm-3.9 cm mature larvae, harvesting the mature larvae of the *Protaetia brevitarsis* Lewis, and replenishing young larvae of the *Protaetia brevitarsis* Lewis meeting conversion conditions.

7. The method of continuously converting kitchen waste using three environmental insects according to claim 2, wherein crop straws used in the method of continuously converting kitchen waste using the three environmental insects are wheat, corn, rice, peanut straw, or vegetable seeding.

* * * * *